United States Patent [19]
Gaa et al.

[11] Patent Number: 5,633,378
[45] Date of Patent: May 27, 1997

[54] POLYALKYLPIPERIDINE COMPOUNDS

[75] Inventors: Karl Gaa, Burtenbach; Matthias Zäh, Gersthofen; Josef Wiedemann, Zusmarshausen, all of Germany

[73] Assignee: Hoechst Aktiengesellschaft, Frankfurt am Main, Germany

[21] Appl. No.: 496,605

[22] Filed: Jun. 29, 1995

[30] Foreign Application Priority Data

Jul. 1, 1994 [DE] Germany .................. 44 23 055.9

[51] Int. Cl.⁶ .................................. C07D 221/20
[52] U.S. Cl. ............. 546/16; 540/466; 540/543; 540/598; 544/209; 544/212; 544/219; 546/14; 546/19; 546/22
[58] Field of Search .................. 544/194, 207, 544/219, 209, 212; 540/466, 543, 598; 546/14, 16, 19, 22

[56] References Cited

U.S. PATENT DOCUMENTS

| | | | |
|---|---|---|---|
| 4,191,684 | 3/1980 | Wiezer et al. | 546/19 |
| 4,220,773 | 9/1980 | Wiezer et al. | 546/19 |
| 4,319,030 | 3/1982 | Wiezer et al. | 546/19 |
| 4,340,534 | 7/1982 | Wiezer et al. | 524/99 |
| 4,405,735 | 9/1983 | Wiezer et al. | 524/95 |
| 4,562,220 | 12/1985 | Wiezer et al. | 524/95 |
| 4,689,416 | 8/1987 | Ertl et al. | 546/19 |
| 4,745,192 | 5/1988 | Ertl | 546/19 |
| 4,755,602 | 7/1988 | Ertl | 546/19 |
| 4,771,091 | 9/1988 | Ertl | 524/97 |
| 5,169,925 | 12/1992 | Schmailzl et al. | 528/367 |

FOREIGN PATENT DOCUMENTS

| | | |
|---|---|---|
| 001207 | 4/1979 | European Pat. Off. |
| 025867 | 4/1981 | European Pat. Off. |
| 0008102 | 9/1981 | European Pat. Off. |
| 0028318 | 12/1982 | European Pat. Off. |
| 095076 | 11/1983 | European Pat. Off. |
| 0057885 | 1/1985 | European Pat. Off. |
| 208263 | 1/1987 | European Pat. Off. |
| 208264 | 1/1987 | European Pat. Off. |
| 208265 | 1/1987 | European Pat. Off. |
| 224181 | 6/1987 | European Pat. Off. |
| 0208263 | 9/1989 | European Pat. Off. |
| 402889 | 12/1990 | European Pat. Off. |
| 3523679 | 1/1986 | Germany . |

*Primary Examiner*—Yogendra N. Gupta
*Attorney, Agent, or Firm*—Connolly and Hutz

[57] ABSTRACT

Polyalkylpiperidine compounds of the formula I

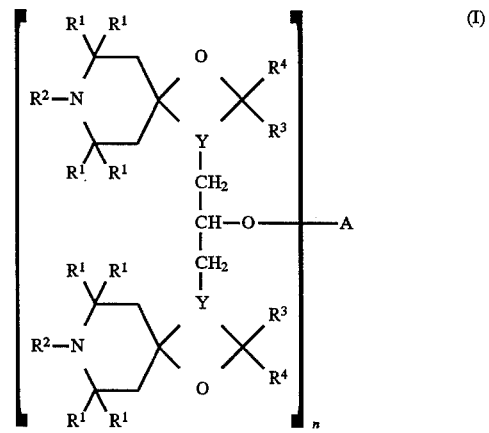

in which Y is the group

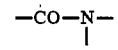

are very effective stabilizers for organic materials.

3 Claims, No Drawings

POLYALKYLPIPERIDINE COMPOUNDS

The present invention relates to novel polyalkylpiperidine compounds which exhibit improvements in virtually all properties.

It is known that organic compounds are damaged by light, radiation, oxygen or heat. There have already been many publications describing compounds for stabilizing organic material. Some of them relate to compounds based on 2,2,6,6-tetramethylpiperidine. Spiro compounds have proven particularly effective here (cf. EP 8 102, EP 28 318 and EP 280 263).

Also known are diazaspirodecanes of the formula

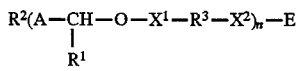

in which $R^1$ is a diazaspirodecyl group (cf. EP 57 885). These compounds have been found to have the disadvantage of being relatively volatile at elevated temperature.

In the search for product properties which have been further improved, it has been found that compounds having a similar structure unexpectedly improve the entire property profile.

The invention thus relates to compounds of the formula I

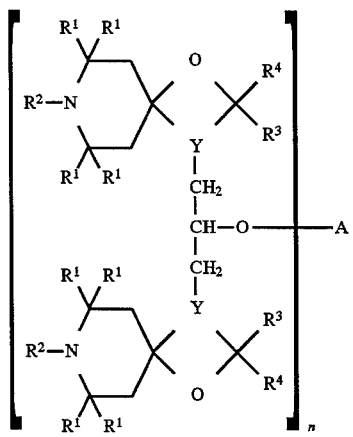

in which Y is the group

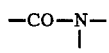

$R^1$ is a hydrogen atom or an alkyl group, $R^2$ is a group of the formula $R^{17}$—O— or $R^{18}$—CO— (acyl), $R^3$ and $R^4$ are identical or different and are a hydrogen atom or an alkyl group, or $R^3$ and $R^4$, together with the carbon atom connecting them, form a ring having 5 to 12 ring members or a group of the formula

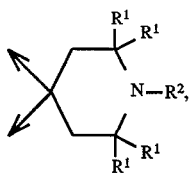

n is 1, 2 or 3, and

A, in the case where n=1, is a hydrogen atom, $R^5$—, $R^5$—CO—, $R^5$—NH—CO— (urethane), —COOR$^5$, —P(OR$^6$) (OR$^7$), —Si(OR$^5$) (OR$^5$) (OR$^5$), —SiR$^5$R$^5$R$^5$ or the

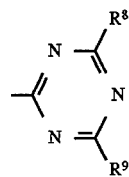

group,

A, in the case where n=2, is —$R^{11}$—, —CO—$R^{12}$—CO—, —CO—NH—$R^{13}$—NH—CO—, —CO—, =POR$^5$, =Si(OR$^5$) (OR$^5$), =SiR$^5$R$^5$ or the

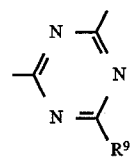

group,

A, in the case where n=3, is $R^{14}$≡, $R^{15}$(CO—)$_3$, $R^{16}$(NH—CO—)$_3$, ≡Si(OR$^5$), ≡SiR$^5$ or the

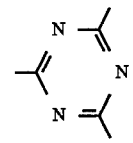

group, $R^5$ is a $C_1$–$C_{18}$-alkyl group, a $C_2$–$C_{18}$-alkenyl group, a $C_2$–$C_{18}$-alkynyl group, a $C_5$–$C_{12}$-cycloalkyl group, a $C_6$–$C_{10}$-bicycloalkyl group, a $C_5$–$C_8$-cycloalkenyl group, a $C_6$–$C_{10}$-aryl group, a $C_7$–$C_9$-aralkyl group, a $C_7$–$C_9$-alkaryl group, unsubstituted or substituted by $C_1$–$C_4$-alkyl or phenyl, where a plurality of radicals $R^5$ may be identical or different, $R^6$ and $R^7$ are identical or different and are a $C_1$–$C_{18}$-alkyl group, a $C_2$–$C_{18}$-alkenyl group, a $C_2$–$C_{18}$-alkynyl group, a $C_5$–$C_{12}$-cycloalkyl group, a $C_6$–$C_{10}$-bicycloalkyl group, a $C_5$–$C_8$-cycloalkenyl group, a $C_6$–$C_{10}$-aryl group, a $C_7$–$C_9$-aralkyl group or a $C_7$–$C_9$-aralkyl group, substituted by $C_1$–$C_4$-alkyl or phenyl, or are a radical of the formula II or III

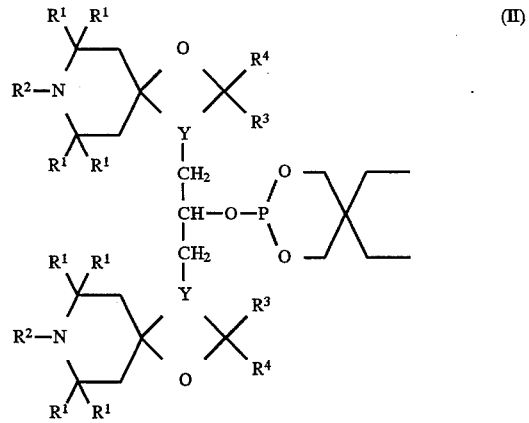

-continued

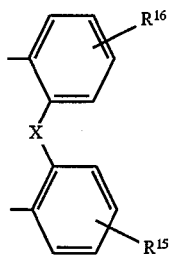

in which $R^1$, $R^2$, $R^3$, $R^4$ and $R^5$ are as defined above, and X is a direct bond or methylene group or a 1,1-alkylidene group having 2 to 5 carbon atoms, $R^8$ and $R^9$ are identical or different and are —$OR^5$, —$NHR^5$, —$NR^{17}R^{18}$ or one of the two groups

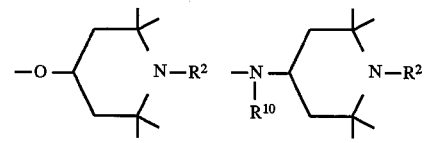

in which $R^{10}$ is a hydrogen atom, a $C_1$–$C_{12}$-alkyl group, a $C_5$–$C_7$-cycloalkyl group, a $C_7$–$C_9$-aralkyl group, a $C_8$–$C_{18}$-alkanoyl group, a $C_3$–$C_5$-alkenoyl group or a benzoyl group, or is

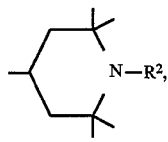

$R^{11}$, $R^{12}$ and $R^{13}$ are identical or different and are a $C_1$–$C_{12}$-alkylene group, a $C_5$–$C_{13}$-cycloalkylene group, a $C_8$–$C_{10}$-bicycloalkylene group, a $C_6$–$C_{10}$-arylene group, a $C_7$–$C_9$-aralkylene group or $C_7$–$C_9$-arylene group, substituted by $C_1$–$C_4$-alkyl or phenyl, $R^{14}$, $R^{15}$ and $R^{16}$ are identical or different and are a trifunctional $C_3$–$C_{18}$-alkyl radical, $C_5$–$C_7$cycloalkyl radical, $C_6$–$C_{10}$-aryl radical or $C_6$–$C_{10}$-aryl radical which is substituted by $C_1$–$C_4$-alkyl or phenyl, $R^{17}$ and $R^{18}$ are identical or different and are a $C_1$–$C_{10}$-alkyl group, a $C_5$–$C_7$-cycloalkyl group or a $C_6$–$C_{10}$-aryl group, or $R^{17}$ and $R^{18}$, together with the nitrogen, form a 5- to 12-membered ring, which may also contain oxygen.

The invention also relates to the preparation of these compounds and to their use for stabilizing organic material, in particular plastics, oils and surface coatings.

In the formula I

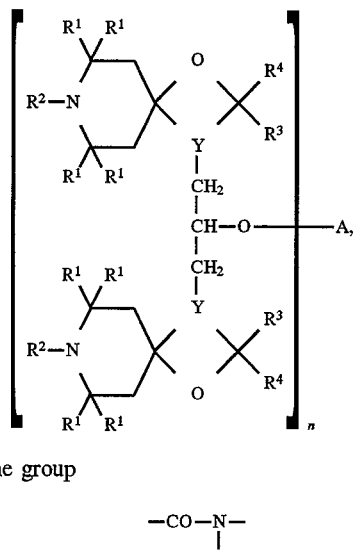

Y is the group $$-CO-N-$$

where the numbers shown indicate the position of the atoms in the spirodecyl five-membered ring. Y is preferably a group in which the oxygen atom is adjacent to the carbon atom common to both rings, i.e.

$$-CO-N-,$$

n is 1, 2 or 3, preferably 1.

$R^1$ is a hydrogen atom or a $C_1$–$C_{18}$-alkyl group, preferably a methyl group.

$R^2$ is one of the groups $R^{17}$—O— and $R^{18}$—CO— (acyl), in which $R^{17}$ and $R^{18}$ are identical or different and are a $C_1$–$C_{18}$-, preferably $C_1$–$C_8$-alkyl group, a $C_5$–$C_7$-cycloalkyl group, or a $C_6$–$C_{10}$-, preferably $C_6$-aryl group, or $R^{17}$ and $R^{18}$, together with the nitrogen, form a 5- to 12-membered ring, preferably a 5- to 6-membered ring, which may also contain oxygen, in particular a pyrrolidine, piperidine or morpholine ring.

$R^3$ and $R^4$ are identical or different and are a hydrogen atom, a $C_1$–$C_{18}$-, preferably $C_1$–$C_8$-alkyl group, or $R^3$ and $R^4$, together with the carbon atom connecting them, form a ring having 5 to 12, preferably 6 or 12, ring members, or, together with the carbon atom connecting them, form a

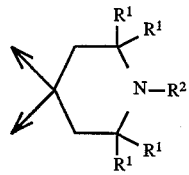

group.

If n=1, A is a hydrogen atom or an $R^5$—, $R^5$—CO—, $R^5$—NH—CO— (urethane), —$COOR^5$, —$P(OR^6)$ $(OR^7)$, —$Si(OR^5)$ $(OR^5)$ $(OR^5)$ or —$SiR^5R^5R^5$ group, in which $R^5$ is as defined above.

$R^5$ is a $C_1$–$C_{18}$-, preferably $C_1$–$C_8$-alkyl group, a $C_2$–$C_{18}$-, preferably $C_3$–$C_6$-alkenyl group, a $C_2$–$C_{18}$-, preferably $C_2$–$C_8$-alkynyl group, a $C_5$–$C_{12}$-, preferably $C_5$–$C_6$-cycloalkyl group, a $C_6$–$C_{10}$-, preferably $C_6$–$C_{10}$-bicycloalkyl group, a $C_5$–$C_8$-, preferably $C_5$–$C_6$-cycloalkenyl group, a $C_6$–$C_{10}$-, preferably $C_6$- or $C_{10}$-aryl group, a $C_7$–$C_9$-aralkyl group, a $C_7$–$C_9$-aralkyl group, substituted by $C_1$–$C_4$-alkyl or phenyl, where a plurality of radicals $R^5$ may be identical or different.

$R^6$ and $R^7$ are identical or different and are a $C_1$–$C_{18}$-, preferably $C_1$–$C_8$-alkyl group, a $C_2$–$C_{18}$-, preferably $C_3$–$C_6$-alkenyl group, a $C_2$–$C_{18}$-, preferably $C_2$–$C_8$-alkynyl group, a $C_5$–$C_{12}$-, preferably $C_5$–$C_6$-cycloalkyl group, a $C_6$–$C_{10}$-, preferably $C_8$–$C_{10}$-bicycloalkyl group, a $C_5$–$C_8$-, preferably $C_5$–$C_6$-cycloalkenyl group, a $C_6$–$C_{10}$-, preferably $C_6$- or $C_{10}$-aryl group, a $C_7$–$C_9$-aralkyl group or a $C_7$–$C_9$-aralkyl group, substituted by $C_1$–$C_4$-alkyl or phenyl, or are a radical of the formula II or III

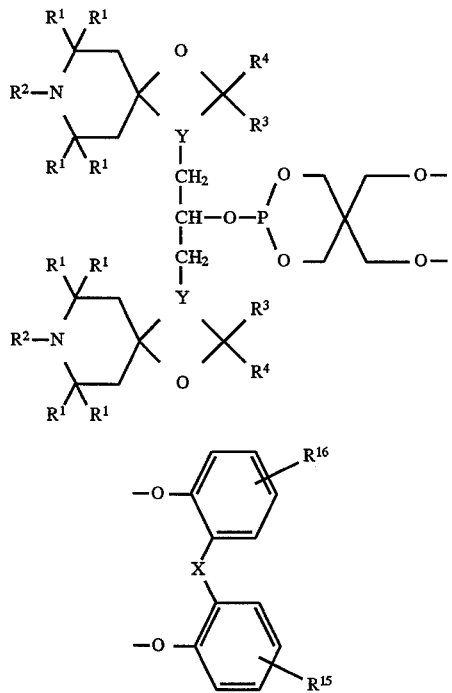

in which $R^1$, $R^2$, $R^3$, $R^4$ and $R^5$ are as defined above, and X is a direct bond or a methylene group or a 1,1-alkylidene group having 2 to 5 carbon atoms, or A is

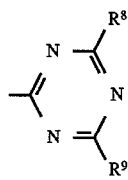

in which $R^8$ and $R^9$ are identical or different and are —$OR^5$, —$NHR^5$, —$NR^{17}R^{18}$ or one of the two groups

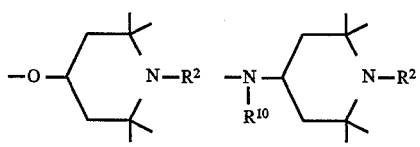

in which $R^{10}$ is a hydrogen atom, a $C_1$–$C_{12}$-, preferably $C_1$–$C_8$-alkyl group, a $C_5$–$C_7$-, preferably $C_5$–$C_6$-cycloalkyl group, a $C_7$–$C_9$-aralkyl group, a $C_8$–$C_{18}$-, preferably $C_2$–$C_8$-alkanoyl group, a $C_3$–$C_5$-, preferably $C_3$–$C_4$-alkenoyl group or a benzoyl group, or is

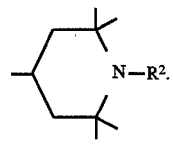

A is preferably a hydrogen atom, $R^5$— or $R^5$—CO—, where $R^5$ is as defined above, in particular $C_1$- to $C_{18}$-acyl, specifically formyl, acetyl, lauryl or stearyl.

If n=2, A is —$R^{11}$—, —CO—$R^{12}$—CO—, —CO—NH—$R^{13}$—NH—CO—, —CO—, =$POR^5$, =$Si(OR^5)(OR^5)$, =$SiR^5R^5R^5$ or the

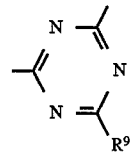

group, in which $R^5$ and $R^9$ are as defined above, and $R^{11}$, $R^{12}$ and $R^{13}$ are identical or different and are a $C_1$–$C_{12}$-, preferably $C_1$–$C_8$-alkylene group, specifically a methylene, ethylene, butylene, hexamethylene or octamethylene group, a $C_5$–$C_{13}$-, preferably $C_5$–$C_6$-cycloalkylene group, specifically a cyclohexylene, 4,4'-dicyclohexylmethylene or isophorone group, a $C_8$–$C_{10}$-, preferably $C_{10}$-bicycloalkylene group, a $C_6$–$C_{10}$-, preferably $C_6$- or $C_{10}$-arylene group, specifically a phenylene or naphthylene group, a $C_7$–$C_9$-aralkylene group or a $C_7$–$C_9$-arylene group, substituted by $C_1$–$C_4$-alkyl or phenyl, in particular tolylene, or a 4,4'-diphenylmethane group.

If n=3, A is $R^{14}\equiv$, $R^{15}(CO—)_3$, $R^{16}(NH—CO—)_3$, $\equiv Si(OR^5)$, $\equiv SiR^5$ or the

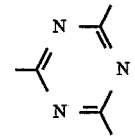

group, where $R^{14}$, $R^{15}$ and $R^{16}$ are identical or different and are a trifunctional $C_3$–$C_{18}$-, preferably $C_3$–$C_8$-alkyl radical, $C_5$–$C_7$-, preferably $C_5$–$C_6$-cycloalkyl radical, $C_6$–$C_{10}$-, preferably $C_6$- or $C_{10}$-aryl radical or $C_6$–$C_{10}$-aryl radical which is substituted by $C_1$–$C_4$-alkyl or phenyl.

The compounds of the formula I in which n=1 and A=H are prepared either by linking compounds of the formula IV

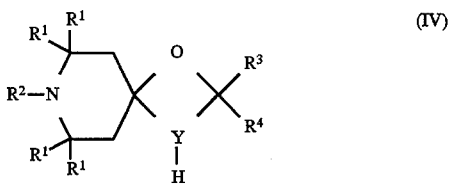

to epichlorohydrin or by reacting compounds of the formula V

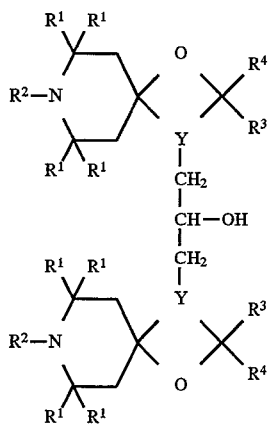 (V)

with the conventional reagents to give the compounds of the formula I containing the desired $R^2$.

The compounds of the formula I in which A is not H can advantageously be prepared by reactions, known per se, of the alcohols of the formula V with the corresponding reactive components of the formula VI $$A + Z]_n \qquad (VI)$$

where

Z is a halogen atom or the $=OR^{17}$ group for $A=R^5$—CO—, —CO—$R^{12}$—CO—, $R^{15}(CO—)_3$, —CO, —COOR$^5$, —P(OR$^6$) (OR$^7$) or =POR$^5$;

Z is a halogen atom for $A=R^5$—, —$R^{11}$—, —Si(OR$^5$) (OR$^5$) (OR$^5$), =Si(OR$^5$) (OR$^5$), ≡Si(OR$^5$), —SiR$^5$R$^5$R$^5$, =SiR$^5$R$^5$, ≡SiR$^5$ or a triazine derivative; and Z is the —NCO group for $A=R^5$—, —$R^{13}$— or $R^{16}$≡.

Another method of preparing the novel compounds of the formula I in which A is not H comprises reacting the compounds I in which $R^2$=H and A is not H with the conventional reagents to give the substituted products 1 in which $R^2$ is not H.

The reaction is carried out in a protic or aprotic, organic solvent, preferably a hydrocarbon, in particular an aromatic hydrocarbon, such as, for example, toluene or xylene, or in mixtures thereof or in an alcohol, preferably an aliphatic alcohol, in particular in a $C_1$–$C_{12}$-alcohol, such as in isopropanol or in a mixture of a hydrocarbon and an alcohol, in particular xylene or isopropanol. Another possibility is to use one of the reaction components in excess as solvent.

If, during the introduction of A,

- hydrogen halide is eliminated, the reaction is carried out in the presence of bases;
- alcohol is eliminated, the reaction is carried out in the presence of catalytic amounts of bases or in the presence of conventional transesterification catalysts;
- an isocyanate is adducted, the reaction can be carried out without any additions.

The reaction is carried out at a temperature of from 20° C. to the boiling point of the solvent; the suitable temperature depends on the base used and on the reactivity of the compound of the formula VI employed.

The novel compounds of the formula I can be in the form of the free bases or as acid-addition salts. Suitable anions are derived, for example, from inorganic acids and in particular from organic acids or sulfonic acids. Examples of inorganic anions are chloride, bromide, sulfate, tetrafluoroborate, phosphate and rhodanide. Suitable carboxylic acids are formate, acetate, propionate, hexanoate, cyclohexanoate, lactate, stearate, acrylate, methacrylate, citrate, malonate and succinate, and anions of polycarboxylic acids containing up to 3000 COOH groups. Examples of sulfonic acid anions are benzenesulfonate and tosylate.

The novel compounds are highly suitable for stabilizing organic material against the action of light, oxygen and heat. They are added to the organic material to be stabilized in a concentration of from 0.001 to 5% by weight, preferably from 0.02 to 1% by weight, based on the organic material, before, during or after its preparation.

The term organic material is taken to mean, for example, precursors for plastics, surface coatings and oils, in particular plastics, surface coatings and oils themselves.

The present invention also relates to organic material, in particular plastics, surface coatings and oils, which has been stabilized against the action of light, oxygen and heat and which contains the compound in the abovementioned concentrations. These organic materials include the following substances:

1. Polymers of mono- and diolefins, for example high-, medium- or low-density polyethylene (which may have been crosslinked), polypropylene, polyisobutylene, poly-1-butene, polymethyl-1-pentene, polyisoprene or polybutadiene, and polymers of cycloolefins, such as, for example, of cyclopentene or norbornene.

2. Mixtures of the polymers mentioned under 1), for example mixtures of polypropylene with polyethylene or with polyisobutylene.

3. Copolymers of mono- and diolefins with one another or with other vinyl monomers, such as, for example, ethylene-propylene copolymers, propylene-1-butene copolymers, propylene-isobutylene copolymers, ethylene-1-butene copolymers, propylene-butadiene copolymers, isobutylene-isoprene copolymers, ethylene-alkyl acrylate copolymers, ethylene-alkyl methacrylate copolymers, ethylene-vinyl acetate copolymers or ethylene-acrylic acid copolymers, and salts thereof (ionomers), and terpolymers of ethylene with propylene and a diene, such as hexadiene, dicyclopentadiene or ethylidenenorbornene.

4. Polystyrene and poly(p-methylstyrene).

5. Copolymers of styrene or α-methylstyrene with dienes or acrylic derivatives, such as, for example, styrene-butadiene, styrene-maleic anhydride, styrene-acrylonitrile, styrene-ethyl methacrylate, styrene-butadiene-ethyl acrylate, styrene-acrylonitrile-methacrylate; high-impact-strength mixtures of styrene copolymers and another polymer, such as, for example, a polyacrylate, a diene polymer or an ethylene-propylene-diene terpolymer; and block copolymers of styrene, such as, for example, styrene-butadiene-styrene, styrene-isoprene-styrene, styrene-ethylene/butylene-styrene or styrene-ethylene/propylene-styrene.

6. Graft copolymers of styrene, such as, for example, styrene on polybutadiene, styrene and acrylonitrile on polybutadiene, styrene and maleic anhydride on polybutadiene, styrene and alkyl acrylates or alkyl methacrylates on polybutadiene, styrene and acrylonitrile on ethylene-propylene-diene terpolymers, styrene and acrylonitrile on polyalkyl acrylates or polyalkyl methacrylates, styrene and acrylonitrile on acrylate-butadiene copolymers, and mixtures thereof with the copolymers mentioned under 5), which are known, for example, as ABS, MBS, ASA or AES polymers.

7. Polyvinyl chloride.

8. Copolymers of vinyl chloride, which can be prepared by known processes (for example suspension, bulk or emulsion polymerization).

9. Copolymers of vinyl chloride containing up to 30% by weight of comonomers, such as, for example, vinyl acetate, vinylidene chloride, vinyl ethers, acrylonitrile, acrylates, maleic monoesters or diesters or olefins, and graft polymers of vinyl chloride.

10. Halogen-containing polymers, such as, for example, polychloroprene, chlorinated rubber, chlorinated or chlorosulfonated polyethylene, epichlorohydrin homopolymers and copolymers, in particular polymers of halogen-containing vinyl compounds, such as, for example, polyvinylidene chloride, polyvinyl fluoride, polyvinylidene fluoride; and copolymers thereof, such as of vinyl chloride-vinylidene chloride, vinyl chloride-vinyl acetate or vinylidene chloride-vinyl acetate.

11. Polymers derived from α,β-unsaturated acids and derivatives thereof, such as polyacrylates and polymethacrylates, polyacrylamides and polyacrylonitriles.

12. Copolymers of the monomers mentioned under 11) with one another or with other unsaturated monomers, such as, for example, acrylonitrile-butadiene copolymers, acrylonitrile-alkyl acrylate copolymers, acrylonitrile-alkoxyacrylate copolymers, acrylonitrile-vinyl halide copolymers or acrylonitrile-alkyl methacrylate-butadiene copolymers.

13. Polymers derived from unsaturated alcohols and amines or acyl derivatives or acetals thereof, such as polyvinyl alcohol, polyvinyl acetate, stearate, benzoate or maleate, polyvinylbutyral, polyallylphthalate and polyallylmelamine.

14. Homopolymers and copolymers of cyclic ethers, such as polyethylene glycols, polyethylene oxide, polypropylene oxide or copolymers thereof with bis-glycidyl ethers.

15. Polyacetals, such as polyoxymethylene, and polyoxymethylenes containing comonomers, such as, for example, ethylene oxide.

16. Polyphenylene oxides and sulfides, and mixtures thereof with styrene polymers.

17. Polyurethanes derived from polyethers, polyesters and polybutadienes containing terminal hydroxyl groups on the one hand and aliphatic or aromatic polyisocyanates on the other hand, and precursors thereof (polyisocyanatepolyol prepolymers).

18. Polyamides and copolyamides derived from diamines and dicarboxylic acids and/or from aminocarboxylic acids or the corresponding lactams, such as nylon 4, nylon 6, nylon 6.6, nylon 6.10, nylon 11, nylon 12, poly-2,4,4-trimethylhexamethyleneterephthalamide, poly-m-phenyleneisophthalamide, and copolymers thereof with polyethers, such as, for example, with polyethylene glycol, polypropylene glycol or polytetramethylene glycol.

19. Polyureas, polyimides and polyamide imides.

20. Polyesters derived from dicarboxylic acids and diols and/or from hydroxycarboxylic acids or the corresponding lactones, such as polyethylene terephthalate, polybutylene terephthalate, poly-1,4-dimethylolcyclohexane terephthalate, poly(2,2-bis(4-hydroxyphenyl)propane) terephthalate, polyhydroxybenzoates, and a block polyetherester derived from polyethylene containing hydroxyl terminal groups, dialcohols and dicarboxylic acids.

21. Polycarbonates and polyester carbonates.

22. Polysulfones, polyether sulfones and polyether ketones.

23. Crosslinked polymers derived from aldehydes on the one hand and phenols, urea or melamine on the other hand, such as phenol-formaldehyde, urea-formaldehyde and melamine-formaldehyde resins.

24. Drying and non-drying alkyd resins.

25. Unsaturated polyester resins derived from copolyesters of saturated and unsaturated dicarboxylic acids with polyhydric alcohols, and vinyl compounds as cross-linking agents, and also halogen-containing, low-combustibility modifications thereof.

26. Crosslinkable acrylic resins derived from substituted acrylates, such as, for example, epoxy acrylates, urethane acrylates or polyester acrylates.

27. Alkyd resins, polyester resins and acrylate resins which have been crosslinked with melamine resins, urea resins, polyisocyanates or epoxy resins.

28. Crosslinkable epoxy resins derived from polyepoxides, for example from bis-glycidyl ethers or from cycloaliphatic diepoxides.

29. Natural polymers, such as cellulose, natural rubber, gelatin or derivatives thereof which have been chemically modified in a polymer-homologous reaction, such as cellulose acetates, propionates and butyrates, or cellulose ethers, such as methyl cellulose.

30. Mixtures of the abovementioned polymers, such as, for example, PP/EPDM, nylon 6/EPDM or ABS, PVC/EVA, PVC/ABS, PVC/MBS, PC/ABS, PBTP/ABS, PC/ASA, PC/PBT, PVC/CPE, PVD/acrylate, POM/thermoplastic PUR, POM/acrylate, POM/MBS, PPE/HIPS, PPE/nylon 6.6 and copolymers, PA/HDPE, PA/PP and PA/PPE.

31. Naturally occurring and synthetic organic substances which are pure monomers or mixtures of monomers, such as, for example, mineral oils, animal and vegetable fats, oils and waxes, or oils, fats and waxes based on synthetic esters, or mixtures of these substances.

32. Aqueous dispersions of natural or synthetic rubber.

The organic material stabilized by means of the novel compounds can, if desired, also contain further additives, for example antioxidants, light stabilizers, metal deactivators, antistatic agents, flame proofing agents, pigments and fillers.

Antioxidants and light stabilizers which can be added in addition to the novel compounds are, for example, compounds based on sterically hindered amines or sterically hindered phenols or sulfur- or phosphorus-containing costabilizers.

Examples of suitable compounds of this type are:

1 Antioxidants 1.1 Alkylated monophenols, for example 2,6-di-t-butyl-4-methylphenol, 2-butyl-4,6-dimethylphenol,2,6-di-t-butyl-4-ethylphenol, 2,6-di-t-butyl-4-n-butylphenol, 2,6-di-t-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-t-butyl-4-methoxymethylphenol,2,6-di-nonyl-4-methylphenol, 2,4-dimethyl-6-(1'-methylundec-1'-yl)-phenol, 2,4-dimethyl-6-(1'-methylheptadec-1'-yl)phenol, 2,4-dimethyl-6-(1'-methyltridec-1'-yl)phenol and mixtures of these compounds 1.2 Alkylthiomethylphenols, for example 2,4-dioctylthiomethyl-6-t-butylphenol, 2,4-dioctylthiomethyl-6-methylphenol, 2,4-dioctylthiomethyl-6-ethylphenol, 2,6-di-dodecylthiomethyl-4-nonylphenol.

1.3 Hydroquinones and alkylated hydroquinones, for example 2,6-di-t-butyl-4-methoxyphenol, 2,5-di-t-butylhydroquinone, hydroquinone, 2,5-di-t-amylhydroquinone, 2,6-diphenyl-4-octadecyloxyphenol, 2,6 -di-t-butylhydroquinone, 2,5-di-t-butyl-4-hydroxyanisole, 3,5-di-t-butyl-4-hydroxyanisole, 3,5-di-t-butyl-4-hydroxyphenyl stearate, bis(3,5-di-t-butyl-4-hydroxyphenyl) adipate.

1.4 Hydroxylated thiodiphenyl ethers, for example 2,2'-thiobis(6-t-butyl-4-methylphenol), 2,2'-thiobis(4-octylphenol), 4,4'-thiobis(6-t-butyl-3-methylphenol), 4,4'-thiobis(6-t-butyl-2-methylphenol), 4,4'-thiobis(3,6-di-sec-amylphenol), 4,4'-bis(2,6-dimethyl-4-hydroxyphenyl) disulfide.

1.5 Alkylidenebisphenols, for example 2,2'-methylenebis (6-t-butyl-4-methylphenol), 2,2'-methylenebis(6-t-butyl-4-ethylphenol), 2,2'-methylenebis-[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-t-butylphenol), 2,2'-ethylidenebis(4,6-di-t-butylphenol), 2,2'-ethylidenebis(6-t-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-t-butylphenol), 4,4'-methylenebis(6-t-butyl-2-methylphenol), 1,1-bis(5-t-butyl-4-hydroxy-2-methylphenyl)butane, 2,6-bis(3-t-butyl-5-methyl-2-hydroxybenzyl)-4-methylphenol, 1,1,3-tris(5-t-butyl-4-hydroxy-2-methylphenyl)butane, 1,1-bis(5-t-butyl-4-hydroxy-2-methyl-phenyl)-3-n-dodecylmercaptobutane, bis (3-t-butyl-4-hydroxy-5-methylphenyl)dicyclopentadiene, bis[2-(3'-t-butyl-2'-hydroxy-5'-methylbenzyl)-6-t-butyl-4-methylphenyl]terephthalate, 1,1-bis(3,5-dimethyl-2-hydroxyphenyl)butane, 2,2-bis(3,5-di-t-butyl-4-hydroxyphenyl)propane, 2,2-bis(5-t-butyl-4-hydroxy-2-methylphenyl)-4-n-dodecylmercaptobutane, 1,1,5,5-tetra-(5-t-butyl-4-hydroxy-2-methylphenyl)pentane.

1.6 O-, N- and S-benzyl compounds, for example 3,5,3', 5'-tetra-t-butyl-4,4'-dihydroxydibenzyl ether, octadecyl 4-hydroxy-3,5-dimethylbenzylmercaptoacetate, tris(3,5-di-t-butyl-4-hydroxybenzyl)amine, bis(4-t-butyl-3-hydroxy-2, 6-dimethylbenzyl) dithioterephthalate, bis(3,5-di-t-butyl-4-hydroxybenzyl) sulfide, isooctyl 3,5-di-t-butyl-4-hydroxybenzylmercaptoacetate.

1.7 Hydroxybenzylated malonates, for example dioctadecyl-2,2-bis(3,5-di-t-butyl-2-hydroxybenzyl) malonate, dioctadecyl 2-(3-t-butyl-4-hydroxy-5-methylbenzyl)malonate, didodecylmercaptoethyl2,2-bis(3, 5-di-t-butyl-4-hydroxybenzyl)malonate.

1.8 Aromatic hydroxybenzyl compounds, for example 1,3,5-tris(3,5-di-t-butyl-4-hydroxybenzyl)-2,4,6-trimethylbenzene, 1,4-bis(3,5-di-t-butyl-4-hydroxybenzyl)-2,3,5,6-tetramethylbenzene, 2,4,6-tris(3,5-di-t-butyl-4-hydroxybenzol)phenol.

1.9 Triazine compounds, for example 2,4-bis (octylmercapto)-6-(3,5-di-t-butyl-4-hydroxyanilino)-1,3,5-triazine, 2-octylmercapto-4,6-bis(3,5-di-t-butyl-4-hydroxyanilino)-1,3,5-triazine, 2-octylmercapto-4,6-bis(3, 5-di-t-butyl-4-hydroxyphenoxy)-1,3,5-triazine, 2,4,6-tris(3, 5-di-t-butyl-4-hydroxyphenoxy)-1,2,3-triazine 1,3,5-tris(3, 5-t-butyl-4-hydroxybenzyl) isocyanurate, 1,3,5-tris(4-t-butyl-3-hydroxy-2,6-dimethylbenzyl)isocyanurate, 2,4,6-tris(3,5-di-t-butyl-4-hydroxyphenylethyl)-1,3,5-triazine, 1,3,5-tris(3,5-di-t-butyl-4-hydroxyphenylpropionyl)-hexahydro-1,3,5-triazine, 1,3,5-tris(3,5-dicyclohexyl-4-hydroxybenzyl) isocyanurate.

1.10 Benzylphosphonates, for example dimethyl 2,5-di-t-butyl-4-hydroxybenzylphosphonate, diethyl 3,5-di-t-butyl-4-hydroxybenzylphosphonate, dioctadecyl 3,5-di-t-butyl-4-hydroxybenzylphosphonate, dioctadecyl 5-t-butyl-4-hydroxy-3-methylbenzyl-phosphonate, calcium ethyl 3,5-di-t-butyl-4-hydroxybenzylphosphonate.

1.11 Acylaminophenols, for example 4-hydroxylauranilide, 4-hydroxystearanilide, octyl N-(3,5-di-t-butyl-4-hydroxyphenyl)carbamate.

1.12 Esters of β-(3,5-di-t-butyl-4-hydroxyphenyl)-5 propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.13 Esters of β-(5-t-butyl-4-hydroxy-3-methylphenyl) propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14 Esters of β-(3,5-dicyclohexyl-4-hydroxyphenyl) propionic acid with mono- or polyhydric alcohols, e.g. with methanol, ethanol, octadecanol, 1,6-hexanediol,1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15 Esters of 3,5-di-t-butyl-4-hydroxyphenylacetic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis (hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16 Esters of 3,3-bis(3'-t-butyl-4'-hydroxyphenyl)butyric acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis (hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17 Amides of β-(3,5-di-t-butyl-4-hydroxyphenyl) propionic acid, e.g. N,N'-bis(3,5-di-t-butyl-4-hydroxyphenylpropionyl)hexamethylenediamine, N,N'-bis (3,5-di-t-butyl-4-hydroxyphenylpropionyl) trimethylenediamine, N,N'-bis(3,5-di-t-butyl-4-hydroxyphenylpropionyl)hydrazine.

2 UV absorbers and light stabilizers 2.1 2-(2'-Hydroxyphenyl)benzotriazoles, for example 2-(2'-hydroxy-5'-methylphenyl)benzotriazole, 2-(3',5'-di-t-butyl-2'-hydroxyphenyl)benzotriazole, 2-(5'-t-butyl-2'-hydroxyphenyl)benzotriazole, 2-[2'-hydroxy-5'-(1,1,3,3-tetramethylbutyl)phenyl]benzotriazole, 2-(3',5'-di-t-butyl-2'-hydroxyphenyl)-5-chlorobenzotriazole, 2-(3'-t-butyl-2'-hydroxy-5'-methylphenyl)-5-chlorobenzotriazole, 2-(3'-sec-butyl-5'-t-butyl-2'-hydroxyphenyl)benzotriazole, 2-(2'-hydroxy-4'-octyloxyphenyl)benzotriazole, 2-(3',5'-di-t-amyl-2'-hydroxyphenyl)benzotriazole, 2-(3',5'-bis(α,α-dimethylbenzyl)-2'-hydroxyphenyl)benzotriazole, mixture of 2-(3'-t-butyl-2'-hydroxy-5'-(2-octyloxycarbonylethyl)-5-chlorobenzotriazole, 2-(3'-t-butyl-5'-[2-(2-ethylhexyloxy)carbonylethyl]-2'-hydroxyphenyl)-5-chlorobenzotriazole, 2-(3'-t-butyl-2'-hydroxy-5'-(2-methoxycarbonylethyl) phenyl)-5-chlorobenzotriazole, 2-(3'-t-butyl-2'-hydroxy-5'-

(2-methoxycarbonylethyl)phenyl)benzotriazole, 2-(3'-t-butyl-2'-hydroxy-5'-(2-octyloxycarbonylethyl)phenyl) benzotriazole, 2-(3'-t-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole, and 2-(3'-t-butyl-2'-hydroxy-5'-(2-isooctyloxycarbonylethyl) phenyl)benzotriazole, 2,2'-methylenebis[4-(1,1,3,3-tetramethylbutyl)-6-benzotriazole-2-yl-phenol]; the transesterification product of 2-[3'-t-butyl-5'-(2-methoxycarbonylethyl)-2'-hydroxyphenyl]benzotriazole with polyethylene glycol 300.

2.2 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-di-methoxy derivatives.

2.3 Esters of substituted and unsubstituted benzoic acids, for example 4-t-butylphenyl salicylate, phenyl salicylate, octylphenyl salicylate, dibenzoylresorcinol, bis(4-t-butylbenzoyl)resorcinol, benzoylresorcinol, 2,4-di-t-butylphenyl 3,5-di-t-butyl-4-hydroxybenzoate, hexadecyl 3,5-di-t-butyl-4-hydroxybenzoate, octadecyl 3,5-di-t-butyl-4-hydroxybenzoate, 2-methyl-4,6-di-t-butylphenyl 3,5-di-t-butyl-4-hydroxybenzoate.

2.4 Acrylates, for example ethyl or isooctyl α-cyano-β, β-diphenylacrylate, methyl α-carbomethoxycinnamate, methyl or butyl α-cyano-β-methyl-p-methoxycinnamate, methyl α-carbomethoxy-p-methoxycinnamate and N-(β-carbomethoxy-β-cyanovinyl)-2-methylindoline.

2.5 Nickel compounds, for example nickel complexes of 2,2-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, such as the methyl or ethyl ester, of 4-hydroxy-3,5-di-t-butylbenzyl-phosphonic acid, nickel complexes of ketoximes, such as of 2-hydroxy-4-methylphenyl undecylketoxime, nickel complexes of 1-phenyl-4-lauroyl-5-hydroxypyrazole, with or without additional ligands.

2.6 Sterically hindered amines, for example bis(2,2,6,6-tetramethylpiperidyl) sebacate, bis(2,2,6,6-tetramethylpiperidyl) glutarate, bis(2,2,6,6-tetramethylpiperidyl) succinate, bis(1,2,2,6,6-pentamethylpiperidyl) sebacate, bis(1,2,2,6,6-pentamethylpiperidyl) glutarate, bis(1,2,2,6,6-pentamethylpiperidyl) n-butyl-3,5-di-t-butyl-4-hydroxybenzylmalonate, 2,2,6,6-tetramethylpiperidyl behenate, 1,2,2,6,6-pentamethylpiperidyl behenate, the condensate of 1-hydroxyethyl-2,2,6,6-tetramethyl-4-hydroxypiperidine and succinic acid, the condensate of N,N'-bis(2,2,6,6-tetramethyl-4-piperidyl) hexamethylenediamine and 4-t-octylamino-2,6-dichloro-1,3,5-s-triazine, tris(2,2,6,6-tetramethyl-4-piperidyl) nitrilotriacetate, tetrakis(2,2,6,6-tetramethyl-4-piperidyl) 1,2,3,4-butanetetraoate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, 4-stearyloxy-2,2,6,6-tetramethylpiperidine, 4-stearyloxy-1,2,2,6,6-pentamethylpiperidine, 4-stearoyloxy-1,2,2,6,6-pentamethylpiperidine, bis(1,2,2,6,6-pentamethylpiperidyl)-2-n-butyl-2-(2-hydroxy-3,5-di-t-butylbenzyl)malonate, bis (1,2,2,6,6-pentamethylpiperidyl) 2-n-butyl-2-(4-hydroxy-3,5-di-t-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl) sebacate, bis(1-octyloxy-2,2,6,6-tetramethylpiperidyl) succinate, the condensate of N,N'-bis (2,2,6,6-tetramethyl-4-piperidyl)hexamethylenediamine and 4-morpholino-2,6-dichloro-1,3,5-triazine, the condensate of 2-chloro-4,6-di(4-n-butylamino-2,2,6,6-tetramethylpiperidyl)-1,3,5-triazine and 1,2-bis(3-aminopropylamino)ethane, the condensate of 2-chloro-4,6-di(4-methoxypropylamino-2,2,6,6-tetramethylpiperidyl)-1,3,5-triazine and 1,2-bis(3-aminopropylamino)ethane, the condensate of 2-chloro-4,6-di(4-methoxypropylamino-1,2,2,6,6-pentamethylpiperidyl)-1,3,5-triazine and 1,2-bis(3-aminopropylamino)ethane, the condensate of 2-chloro-4,6-di(4-n-butylamino-1,2,2,6,6-pentamethylpiperidyl)-1,3,5-triazine and 1,2-bis(3-aminopropylamino)ethane, the products of the reaction of 2-chloro-4,6-di(4-n-butylamino-2,2,6,6-tetramethylpiperidyl)-1,3,5-triazine with mono- or polyamines, where between one and all the active H atoms on the amine are replaced, such as with ethylenediamine, diethylenetriamine, triethylenetetramine, hexamethylenediamine or 1,2-bis(3-aminopropylamino) ethane, the products of the reaction of 2-chloro-4,6-di(4-n-butylamino-1,2,2,6,6-pentamethylpiperidyl)-1,3,5-triazine with mono- or polyamines, where between one and all the active H atoms on the amine are replaced, such as with ethylenediamine, diethylenetriamine, triethylenetetramine, hexamethylenediamine or 1,2-bis(3-aminopropylamino)ethane, the products of the reaction of 2-chloro-4,6-di(4-n-butylamino-2,2,6,6-tetramethylpiperidyl)-1,3,5-triazine and 4-t-octylamino-2,6-dichloro-1,3,5-s-triazine with mono- or polyamines, where between one and all the active H atoms on the amine are replaced, such as with ethylenediamine, diethylenetriamine, triethylenetetramine, hexamethylenediamine or 1,2-bis(3-aminopropylamino)ethane, the products of the reaction of 2-chloro-4,6-di(4-n-butylamino-1,2,2,6,6-pentamethylpiperidyl)-1,3,5-triazine and 4-t-octylamino-2,6-dichloro-1,3,5-s-triazine with mono- or polyamines, where between one and all the active H atoms on the amine are replaced, such as with ethylenediamine, diethylenetriamine, triethylenetetramine, hexamethylenediamine or 1,2-bis(3-aminopropylamino)ethane, the products of the reaction of 2-chloro-4,6-di(4-n-butylamino-2,2,6,6-tetramethylpiperidyl)-1,3,5-triazine and 4-(4-n-butylamino-2,2,6,6-tetramethylpiperidyl)- 2,6-dichloro-1,3,5-s-triazine with mono- or polyamines, where between one and all the active H atoms on the amine are replaced, such as with ethylenediamine, diethylenetriamine, triethylenetetramine, hexamethylenediamine or 1,2-bis(3-aminopropylamino) ethane, the products of the reaction of 2-chloro-4,6-di(4-n-butylamino-1,2,2,6,6-pentamethylpiperidyl)-1,3,5-triazine and 4-(4-n-butylamino-2,2,6,6-tetramethylpiperidyl)-2,6-dichloro-1,3,5-s-triazine with mono- or polyamines, where between one and all the active H atoms on the amine are replaced, such as with ethylenediamine, diethylenetriamine, triethylenetetramine, hexamethylenediamine or 1,2-bis(3-aminopropylamino)ethane, 3-dodecyl-7,7,9,9-tetramethyl-1,3,8-triazaspiro[4,5]decane-2,4-dione, oligomerized 2,2,4, 4-tetramethyl-20-(oxiranylmethyl)-7-oxa-3,20-diazadispiro [5.1.11.2]heneicosan-21-one, oligomerized 1,2,2,4,4-pentamethyl-20-(oxiranylmethyl)-7-oxa-3,20-diazadispiro [5.1.11.2]heneicosan-21-one, oligomerized 1-acetyl-2,2,4,4-tetramethyl-20-(oxiranylmethyl)-7-oxa-3,20-diazadispiro [5.1.11.2]heneicosan-21-one, dodecyl-1-(2,2,4,4-tetramethyl-4-piperidyl)pyrrolidine-2,5-dione, 3-dodecyl-1-(1,2,2,6,6-pentamethyl-4-piperidyl)pyrrolidine-2,5-dione, 2,2,4,4-tetramethyl-7-oxa-3,20-diazadispiro[5.1.11.2] heneicosan-21-one, dodecyl 2,2,4,4-tetramethyl-7-oxa-21-oxo-3,20-diazadispiro[5.1.11.2]heneicosane-3-propanoate, tetradecyl 2,2,4,4-tetramethyl-7-oxa-21-oxo-3,20-diazadispiro[5.1.11.2]heneicosane-3-propanoate, 2,2,3,4,4- pentamethyl-7-oxa-3,20-diazadispiro[5.1.11.2]heneicosan-21-one, dodecyl 2,2,3,4,4-pentamethyl-7-oxa-21-oxo-3,20-diazadispiro[5.1.11.2]heneicosane-3-propanoate, tetradecyl 2,2,3,4,4-pentamethyl-7-oxa-21-oxo-3,20-diazadispiro [5.1.11.2]heneicosane-3-propanoate, 3-acetyl-2,2,4,4-tetramethyl-7-oxa-3,20-diazadispiro[5.1.11.2]-heneicosan-21-one, dodecyl 3-acetyl-2,2,4,4-tetramethyl-7-oxa-21-oxo-3,20-diazadispiro[5.1.11.2]heneicosane-3-propanoate, tetradecyl 3-acetyl-2,2,4,4-tetramethyl-7-oxa-21-oxo-3,20-diazadispiro[5.1.11.2]heneicosane-3-propanoate, 1,1',3,3',5,5'-hexahydro-2,2',4,4',6,6'-hexaaza- 2,2',6,6'-bismethano-7,8-dioxo-4,4'-bis(1,2,2,6,6-pentamethyl-4-piperidyl) biphenyl, poly-N,N'-bis(2,2,6,6-tetramethyl-4-piperidyl)-1,8-diazadecylene, the addition compound of 2,2,6,6-tetramethyl-4-allyloxy-5 piperidine and polymethylhydrosiloxane (molecular weight up to 4000), the addition compound of 1,2,2,6,6-pentamethyl-4-allyloxypiperidine and polymethylhydrosiloxane (molecular weight up to 4000), N,N'-diformyl-N,N'-bis(2,2,6,6-tetramethyl-4-piperidyl) hexamethylenediamine, N,N'-diformyl-N,N'-bis(1,2,2,6,6-pentamethyl-4-piperidyl) hexamethylenediamine, 5,11-bis(2,2,6,6-tetramethyl-4-piperidyl)-3,5,7,9,11,13-hexaazatetracyclo[7.4.0.0.$^{2,7}$.1$^{3,13}$] tetradecane-8,14-dione, 5,11-bis(1,2,2,6,6-pentamethyl-4-piperidyl)-3,5,7,9,11,13-hexaazatetracyclo [7.4.0.0$^{2,7}$.1$^{3,13}$]tetradecane-8,14-dione, 7,7,9,9-tetramethyl-8-acetyl-3-dodecyl-1,3,8-triazaspiro[4.5]decane-2,4-dione, bis(2,2,6,6-tetramethyl-4-piperidyl) [(4-methoxyphenyl)methylene] propanedioate, bis(1,2,2,6,6-pentamethyl-4-piperidyl) [(4-methoxyphenyl)methylene]propanedioate, 2,4,6-tris(N-cyclohexyl-N-[2-(3,3,4,5,5-pentamethylpiperazinon-1-yl) ethyl]amino)-1,3,5-triazine, copolymer of styrene with α-methylstyrene and maleic anhydride reacted with 4-amino-2,2,6,6-tetramethylpiperidine and octadecylamine, copolymer of styrene with α-methylstyrene and maleic anhydride reacted with 4-amino-1,2,2,6,6-pentamethylpiperidine and octadecylamine, polycarbonate with 2,2'-[(2,2,6,6-tetramethyl-4-piperidyl)imino]bisethanol as diol component, polycarbonate with 2,2'-[(1,2,2,6,6-pentamethyl-4-piperidyl)imino]bisethanol as diol component, copolymer of maleic anhydride and an α-olefin having up to 30 carbon atoms reacted with 4-amino-2,2,6,6-tetramethylpiperidine, copolymer of maleic anhydride and an α-olefin having up to 30 carbon atoms reacted with 1-acetyl-4-amino-2,2,6,6-tetramethylpiperidine, copolymer of maleic anhydride and an α-olefin having up to 30 carbon atoms reacted with 4-amino-1,2,2,6,6-pentamethylpiperidine, and the N-alkyl- and N-aryloxy derivatives of the abovementioned compounds containing free NH groups on the piperidine, specifically α-methylbenzoxy and $C_1$ to $C_{18}$- alkoxy.

2.7 Oxalamides, for example 4,4'-dioctyloxyoxanilide, 2,2'-dioctyloxy-5,5'-di-t-butoxanilide, 2,2'-didode-5 cyloxy-5,5'-di-t-butoxanilide, 2-ethoxy-2'-ethoxanilide, N,N'-bis(3-dimethylaminopropyl)oxalamide, 2-ethoxy-5-t-butyl-2'-ethoxanilide and its mixture with 2-ethoxy-2'-ethyl-5,4'-di-t-butoxanilide and mixtures of ortho- and paramethoxy and of o- and p-ethoxy-disubstituted oxanilides.

2.8 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis (2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis (2,4-dimethylphenyl)-1,3,5-triazine, 2-[2-hydroxy-4-(2-hydroxy-3-butyloxy-propoxy)phenyl]-4,6-bis(2,4-dimethylphenyl)-1,3,5-triazine, 2-[2-hydroxy-4-(2-hydroxy-3-octyloxy-propoxy)phenyl]-4,6-bis(2,4-dimethylphenyl)-1,3,5-triazine, 3 Metal deactivators, for example N,N'-diphenyloxamide, N-salicylal-N'-salicyloyl-hydrazine, N,N'-bis(salicyloyl) hydrazine, N,N'-bis(3,5-di-t-butyl-4-hydroxyphenyl-propionyl)hydrazine, 3-salicyloylamino-1,2,4-triazole, bis (benzylidene)oxalyl dihydrazide, oxanilide, isophthaloyl dihydrazide, sebacoyl hisphenylhydrazide, N,N'-diacetyladipodihydrazide, N,N'-bis(salicyloyl)oxalyl dihydrazide, N,N'-bis(salicyloyl)thiopropionyl dihydrazide.

4 Phosphites and phosphonites, for example triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-t-butylphenyl) phosphite, diisodecyl pentaerythritol diphosphite, bis(2,4-di-t-butylphenyl) pentaerythritol diphosphite, bis(2,6-di-t-butyl-4-methylphenyl)-pentaerythritol diphosphite, bis-isodecyloxypentaerythritol diphosphite, bis(2,4-di-t-butyl-6-methylphenyl) pentaerythritol diphosphite, bis(2,4,6-tri-t-butylphenyl) pentaerythritol diphosphite, tristearyl sorbitol triphosphite, tetrakis-(2,4-di-t-butylphenyl) 4,4'-biphenylene diphosphonite, 6-isooctyloxy-2,4,8,10-tetra-t-butyl-12H-dibenzo[d,g]-1,3, 2-dioxaphosphocine, 6-fluoro-2,4,8,10-tetra-t-butyl-12-methyl-dibenzo [d,g]-1,3,2-dioxaphosphocine, bis(2,4-di-t-butyl-6-methylphenyl) methyl phosphite, bis(2,4-di-t-butyl-6-methylphenyl) ethyl phosphite, tris(2-t-butyl-4-thio(2'-methenyl-4'-hydroxy-5'-t-butyl)phenyl-5-methenyl) phenyl phosphite.

5 Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc alkyldithiocarbamates, zinc dibutyldithiocarbamate, dioctadecyl monosulfide, dioctadecyl disulfide, pentaerythritol tetrakis(β-dodecylmercapto)propionate.

6 Polyamide stabilizers, for example copper salts in combination with iodides and/or phosphorus compounds and salts of divalent manganese.

7 Basic costabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmirate, antimony pyrocatecholate or tin pyrocatecholate.

8 Nucleating agents, for example 4-t-butylbenzoic acid, adipic acid, diphenylacetic acid.

9 Fillers and reinforcing agents, for example calcium carbonate, silicates, glass fibers, asbestos, talc, kaolin, mica, barium sulfate, metal oxides and hydroxides, carbon black and graphite.

10 Other additives, for example plasticizers, lubricants, emulsifiers, pigments, optical brighteners, flameproofing agents, antistatic agents and blowing agents.

The additives are incorporated into the organic polymers by generally conventional methods. For example, the incorporation can be effected by mixing or applying the compounds and, if desired, further additives into or onto the polymer directly after the polymerization or into the melt before or during the shaping. The incorporation can also be carried out by applying the dissolved or dispersed compounds to the polymer directly or by mixing into a solution, suspension or emulsion of the polymer, if necessary subsequently allowing the solvent to evaporate. The compounds are also effective if they are subsequently introduced into a pre-granulated polymer in a separate processing step.

The compounds used in accordance with the invention can also be added to the polymers to be stabilized in the form of a masterbatch containing these compounds, for example, in a concentration of from 1 to 75% by weight, preferably from 2.5 to 30% by weight.

The examples below are intended to illustrate the invention in greater detail.

A particularly suitable method for characterizing the compounds, which do not crystallize, is the shift in signals in the $^1$H-NMR. Reaction of the alcohol function on the 2-hydroxy-1,3-propanediyl structural unit causes the $^1$H-NMR signal on $C^2$ to shift significantly ($-C^1H_2-C^2H$(OH)$-C^3H_2-$). For characterization of the compounds, either the shift of this $^1$H-NMR signal or another characteristic signal in the $^1$H-NMR is given.

EXAMPLE 1

20,20'-(2-Hydroxy-1,3-propanediyl)bis[3-(1'-methylbenzoxy)-2,2,4,4,-tetramethyl-7-oxa-3,20-diazadispiro[5.1.11.2]heneicosan-21-one]

78.3 g of 20,20'-(2-hydroxy-1,3-propanediyl)bis[2,2,4,4-tetramethyl-7-oxa-3,20-diazadispiro[5.1.11.2]heneicosan-21-one] and 3.0 g of molybdenum trioxide were introduced into 500 cm³ of ethylbenzene. Under a protective gas, 96.6 g of a 70% strength t-butyl hydroperoxide solution were slowly added dropwise at 110° C. All the water was then removed by azeotropic distillation, and the mixture was boiled for a further 8 hours. The molybdenum trioxide was filtered off, excess peroxide was destroyed, and the solution was washed by shaking with water and dilute hydrochloric acid. After drying, the ethylbenzene was removed by distillation, leaving 100.1 g of the target compound as a pale yellow resin. In the $^1$H-NMR, the >N—O—CH— signal appeared as a quartet at about 4.75 ppm relative to TMS.

EXAMPLE 2

20,20'-(2-Hydroxy-1,3-propanediyl)bis[3-octyloxy-2,2,4,4-tetramethyl-7-oxa-3,20-diazadispiro[5.1.11.2]heneicosan-21-one]

The procedure was as described under Example 1, but n-octane was employed instead of ethylbenzene. Distillation left 101.1 g of the product as a pale yellow, glassy material. The >N—O—CH— atoms were poorly resolved in the $^1$H-NMR at from 3.4 to 3.9 ppm relative to TMS.

EXAMPLE 3

20,20'-(2-Hydroxy-1,3-propanediyl)bis[3-(1'-methylbenzoxy)-2,2,4,4,-tetramethyl-7-oxa-3,20-diazadispiro[5.1.11.2]heneicosan-21-one]

48.5 g of 3-(1'-methylbenzoxy)-2,2,4,4-pentamethyl-7-oxa-3,20-diazadispiro[5.1.11.2]heneicosan-21-one were introduced into 125 cm³ of toluene at 70° C., and 4.0 g of 50% strength sodium hydroxide solution were added. The temperature was then increased to 90° C., 4.6 g of epichlorohydrin and subsequently a further 36 g of 50% strength sodium hydroxide solution were added. The reaction mixture was boiled for 8 hours, 150 cm³ of water were added, and the mixture was heated for a further hour. The steps of addition of 150 cm³ of water followed by refluxing for 1 hour were repeated twice. The phases were separated, and the organic phase was washed by shaking with water, dried and evaporated, leaving 47.6 g of a clear, glassy material of the same compound as described under Example 1.

EXAMPLE 4

20,20'-(2-Hydroxy-1,3-propanediyl)bis[3-octyloxy-2,2,4,4-tetramethyl-7-oxa-3,20-diazadispiro[5.1.11.2]heneicosan-21-one]

The procedure was as described under Example 3, but 49.3 g of 3-octyloxy-2,2,4,4-pentamethyl-7-oxa-3,20-diazadispiro[5.1.11.2]heneicosan-21-one were employed for the reaction. 47.0 g of the same compound as described in Example 2 were obtained as a yellow resin.

EXAMPLE 5

20,20'-(2-Methoxy-1,3-propanediyl)bis[3-(1'-methylbenzoxy)-2,2,4,4,-tetramethyl-7-oxa-3,20-diazadispiro[5.1.11.2]heneicosan-21-one]

0.56 g of sodium hydride were introduced into 30 cm³ of toluene. At 100° C., a solution of 20.5 g of 20,20'-(2-hydroxy-1,3-propanediyl)bis[3-(1'-methylbenzoxy)-2,2,4,4-tetramethyl-7-oxa-3,20-diazadispiro[5.1.11.2]heneicosan-21-one] in 50 cm³ of toluene was slowly added dropwise, and the mixture was stirred for 1 hour. 2.8 g of dimethyl sulfate in 20 cm³ of toluene were likewise added dropwise at this temperature, and the batch was boiled for a further 5 hours. The batch was then poured into water, and the organic phase was separated off and washed by shaking with water. Drying and removal of the solvent by distillation left 19.6 g of the target product as a glassy material. In the $^1$H-NMR, the —O—CH$_3$ signal appeared at about 3.35 ppm.

EXAMPLE 6

20,20'-(2-Methoxy-1,3-propaneallyl)bis[3-(1'-octyloxy)-2,4,4-tetramethyl-7-oxa-3,20-diazadispiro[5.1.11.2]heneicosan-21-one]

The procedure was as described under Example 5, but the 2-methylbenzoxy compound was replaced by 20.8 g of 3-octyloxy-2,2,4,4-tetramethyl-7-oxa-3,20-diazadispiro[5.1.11.2]heneicosan-21-one. 15.2 g of a yellowish resin were obtained. In the $^1$H-NMR, the —O—CH$_3$ signal appeared at about 3.4 ppm.

EXAMPLE 7

0,20'-(2-Benzoxy-1,3-propanediyl)bis[3-(1'-methylbenzoxy)-2,2,4,4-tetramethyl-7-oxa-3,20-diazadispiro[5.1.11.2]heneicosan-21-one]

The procedure was as described under Example 5, but the dimethyl sulfate was replaced by 3.8 g of benzyl bromide. Work-up gave 19.0 g of a pale brown, glassy material. The benzylic —O—CH$_2$— group appeared at about 4.5 ppm in the $^1$H-NMR.

EXAMPLE 8

20,20'-(2-Benzoxy-1,3-propanediyl)bis[3-(octyloxy)-2,2,4,4-tetramethyl-7-oxa-3,20-diazadispiro[5.1.11.2]-heneicosan-21-one]

The procedure was as described under Example 7, but the 1'-methylbenzoxy compound was replaced by 20.8 g of 20,20'-(2-hydroxy-1,3-propanediyl)bis[3-octyloxy-2,2,4,4- tetramethyl-7-oxa-3,20-diazadispiro[5.1.11.2]heneicosan-21-one]. 18.8 g of a pale brown product were obtained. In the ¹H-NMR, the benzylic —O—CH₂ signal appeared at about 4.5 ppm.

EXAMPLE 9

20,20'-(2-Acetoxy-1,3-propanediyl)bis[3-(1'-methylbenzoxy)-2,2,4,4-tetramethyl-7-oxa-3,20-diazadispiro[5.1.11.2]heneicosan-21-one]

20.5 g of 20,20'-(2-hydroxy-1,3-propanediyl)bis[3-(1'-methylbenzoxy)-2,2,4,4-tetramethyl-7-oxa-3,20-diazadispiro[5.1.11.2]heneicosan-21-one] were dissolved in 100 cm³ of acetic anhydride. Over the course of 6 hours, about 50 cm³ of the solvent were removed by distillation as a mixture with the acetic acid formed. The mixture was then evaporated to dryness in vacuo, leaving 19.3 g of the target compound, but still containing traces of acetic anhydride and acetic acid. These were removed by dissolving the product in methyl t-butyl ether and washing by shaking with dilute sodium hydrogencarbonate solution and water. Re-evaporation of the batch gave 17.5 g of the target acetyl compound as a colorless, glassy material. The acetyl CH₃ group appeared at about 2.0 ppm in the ¹H-NMR.

EXAMPLE 10

20,20'-(2-Acetoxy-1,3-propanediyl)bis[3-(octyloxy)-2,2,4,4-tetramethyl-7-oxa-3,20-diazadispiro[5.1.11.2]-heneicosan-21-one]

The procedure was as described under Example 9, but using 20.8 g of 20,20'-(2-hydroxy-1,3-propanediyl)bis[3-5 octyloxy-2,2,4,4-tetramethyl-7-oxa-3,20-diazadispiro[5.1.11.2]heneicosan-21-one] instead of the 1'-methylbenzoxy compound. 18.6 g of a colorless resin were obtained. In the ¹H-NMR, the acetyl CH₃ signal appeared at about 2.0 ppm.

EXAMPLE 11

20,20'-(2-Benzoyloxy-1,3-propanediyl)bis[3-(1'-methylbenzoxy)-2,2,4,4-tetramethyl-7-oxa-3,20-diazadispiro[5.1.11.2]heneicosan-21-one]

20.5 g of 20,20'-(2-hydroxy-1,3-propanediyl)bis[3-(1'-methylbenzoxy)-2,2,4,4-tetramethyl-7-oxa-3,20-diazadispiro[5.1.11.2]heneicosan-21-one] were introduced into 60 cm³ of toluene, and 14 cm³ of 1.6 molar butyllithium solution were carefully added. After 1 hour, 3.1 g of benzoyl chloride in 20 cm³ of toluene were added dropwise, and the mixture was stirred for a further 4 hours. Water was added to the batch, and the organic phase was washed several times by shaking with water, dried and evaporated, leaving 20.0 g of product (signal shift in ¹H-NMR from 3.9 to about 5.6 ppm).

EXAMPLE 12

20,20'-(2-Benzoyloxy-1,3-propaneallyl)bis[3-(octyloxy)-2,2,4,4,-tetramethyl-7-oxa-3,20-diazadispiro[5.1.11.2]-heneicosan-21-one]

The procedure was as described under Example 11, but using 20.8 g of 20,20'-(2-hydroxy-1,3-propanediyl)bis[3-octyloxy-2,2,4,4-tetramethyl-7-oxa-3,20-diazadispiro [5.1.11.2]heneicosan-21-one], giving 21.5 g of pale yellow product (shift in the ¹H-NMR from 3.9 to 5.6 ppm).

Repeating Examples 11 and 12 gave further novel compounds shown in the table below: for n=2, only 50 mol % of component AZ$_n$ with respect to the alcohol are employed.

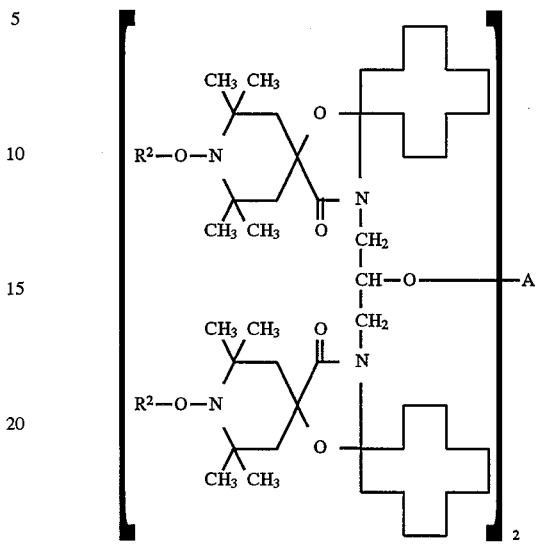

TABLE 1

| Ex. | R² | n | A | ¹H-NMR[1] |
|---|---|---|---|---|
| 13 | 1-Methylbenzyl | 1 | Pivaloyl | 5.25 |
| 14 | 1-Methylbenzyl | 2 | Adipinoyl | 5.35 |
| 15 | 1-Methylbenzyl | 1 | Methoxycarbonyl | 5.3 |
| 16 | 1-Methylbenzyl | 1 | Trimethylsilyl | 4.45 |
| 17 | 1-Methylbenzyl | 1 | ![P(O)(O)] | 4.9 |
| 18 | 1-Methylbenzyl | 1 | —P(—O—C₆H₅)₂ | [2] |
| 19 | Octyl | 1 | Pivaloyl | 5.3 |
| 20 | Octyl | 2 | Adipinoyl | 5.4 |
| 21 | Octyl | 1 | Methoxycarbonyl | 5.3 |
| 22 | Octyl | 2 | Carbonyl | 5.2 |
| 23 | Octyl | 1 | Trimethylsilyl | 4.45 |
| 24 | Octyl | 2 | Dimethylsilyl | 4.35 |
| 25 | Octyl | 1 | ![P(O)(O)] | 4.9 |
| 26 | Octyl | 1 | —P(—O—C₆H₅)₂ | [3] |

[1]: Shift in the ¹H-NMR from 3.9 ppm to
[2]: Hydrogen atoms of the aromatic ring between 6.9 and 7.3 ppm
[3]: Hydrogen atoms of the aromatic ring between 6.9 and 7.4 ppm Further novel compounds are obtained by reacting the alcohols with isocyanates:

EXAMPLE 27

15.4 g of 20,20'-(2-hydroxy-1,3-propanediyl)bis[3-(1'-methylbenzoxy)-2,2,4,4-tetramethyl-7-oxa-3,20-diazadispiro[5.1.11.2]heneicosan-21-one] were dissolved in 60 cm³ of toluene, and 2.15 g of phenyl isocyanate were added. The batch was then refluxed for 24 hours, and the solvent was removed by vacuum distillation, leaving 16.9 g of the target compound as a pale yellow, glassy compound. In the IR spectrum, the carbonyl band of the urethane group appeared at about 1735 cm⁻¹.

Further novel compounds were prepared analogously to Example 27 by reaction with isocyanates (reactions with 1,6-diisocyanatohexane in the molar ratio 2:1):

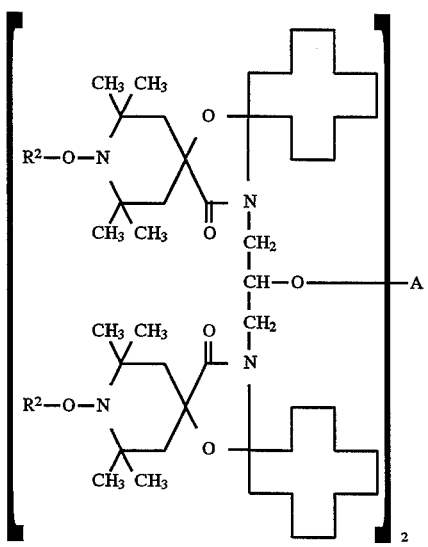

TABLE 2

| Ex. | R² | n | A | IR[1] |
|---|---|---|---|---|
| 28 | 1-Methylbenzyl | 1 | Cyclohexyl | 1720[2] |
| 29 | 1-Methylbenzyl | 2 | Hexamethylene | 1720[2] |
| 30 | Octyl | 1 | Phenyl | 1735 |
| 31 | Octyl | 1 | Cyclohexyl | 1720[2] |
| 32 | Octyl | 2 | Hexamethylene | 1720[2] |

1): Characterization through the position of the urethane carbonyl group in the IR spectrum in cm⁻¹
2): As shoulder

EXAMPLE 33

20,20'-(2-Acetoxy-1,3-propanediyl)bis[3-acetyl-2,2,4,4-tetramethyl-7-oxa-3,20-diazadispiro[5.1.11.2]heneicosan-21-one]

39.2 g of 20,20'-(2-hydroxy-1,3-propanediyl)bis[2,2,4,4-tetramethyl-7-oxa-3,20-diazadispiro[5.1.11.2]heneicosan-21-one] were dissolved in 400 cm³ of acetic anhydride and heated so strongly that about 200 cm³ of liquid distilled off over the course of 6 hours. The batch was then evaporated to dryness in vacuo, the residue was taken up in toluene and washed by shaking with dilute hydrogencarbonate solution and water, and the organic phase was dried. After evaporation, the target compound crystallized as a colorless solid during stirring with hexane. 36.9 g having a melting point of 122° C. were obtained.

EXAMPLE 34

20,20'-(2-Trimethylsilyloxy-1,3-propanediyl)bis[3-acetyl-2,2,4,4-tetramethyl-7-oxa-3,20-diazadispiro[5.1.11.2]-heneicosan-21-one]

The procedure was as described in Example 16. 43.4 g of 20,20'-(2-hydroxy-1,3-propanediyl)bis[3-acetyl-2,2,4,4-tetramethyl-7-oxa-3,20-diazadispiro[5.1.11.2]heneicosan-21-one] and 5.9 g of chlorotrimethylsilane gave 42.2 g of a yellowish, glassy product.

EXAMPLE 35

20,20'-(2-Phenylaminocarbonyloxy-1,3-propanediyl)bis[3-acetyl-2,2,4,4-tetramethyl-7-oxa-3,20-diazadispiro[5.1.11.2]heneicosan-21-one]

The procedure was as described in Example 27. 43.4 g of 20,20'-(2-hydroxy-1,3-propanediyl)bis[3-acetyl-2,2,4,4-tetramethyl-7-oxa-3,20-diazadispiro[5.1.11.2]heneicosan-21-one] and 6.3 g of phenyl isocyanate gave 36.4 g of the target compound as a pale yellow, glassy material.

EXAMPLE 36

Solubility in Hexane

| | Solubility in hexane at room temperature |
|---|---|
| Comp. A (EP 57 885, Ex. 16) | <1% by weight |
| Ex. 1 | >30% by weight |
| Ex. 2 | >30% by weight |
| Ex. 35 | approx. 5% by weight |

EXAMPLE 37

Light-stabilizing action 100 parts by weight of polypropylene having an MFI 230/5 of 3 g/10 min and a density of 0.903 g/cm³ were compounded for 5 minutes at 200° C. with 0.2 part by weight of calcium stearate, 0.1 part by weight of pentaerythrityl tetrakis [3-(3,5-di-t-butyl-4-hydroxyphenyl) propionate], 0.1 part by weight of tris(2,4-di-t-butylphenyl) phosphite and 0.2 part by weight of the stabilizer to be tested. A 150 μm thick film was pressed from this mixture at 190° C. and exposed in a weathering tester (®Xenotest 1200). The criterion selected was the drop in elongation at break to 50%.

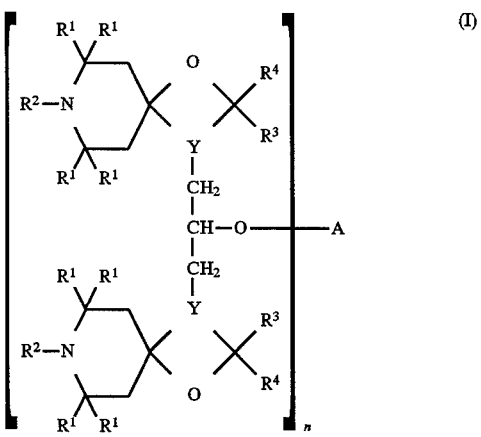

(I)

| | $R^2 =$ | $A =$ | Drop in elongation at break to 50% |
|---|---|---|---|
| Ex. from EP 57 885 | | | |
| (Comp. B) | H | $C_6H_5$—NH—CO | 315 h |
| Ex. 1 | $C_6H_5$—CH ($CH_3$)—O— | $C_6H_5$—NH—CO | 375 h |
| Ex. 2 | $C_8H_{17}$—O— | $C_6H_5$—NH—CO | 390 h |
| Ex. 35 | $CH_3$—CO— | $C_6H_5$—NH—CO | 380 h |

EXAMPLE 38

Stabilizing action in the WAB test

The same mixture as in Example 37 was granulated by means of an extruder at from 200° to 230° C. The granules were converted into injection-molded sheets with a thickness of 1 mm from 210° to 240° C. These sheets were stored at a temperature of 140° C., and the mechanical embrittlement was measured as the criterion. The abbreviations X and Y relate to the formula in Example 37.

| | $R^2 =$ | $A =$ | Mechanical embrittlement |
|---|---|---|---|
| Ex. from EP 57 885 | | | |
| (Comp. C) | H | $C_6H_5$—NH—CO | 43 d |
| Ex. 1 | $C_6H_5$—CH ($CH_3$)—O— | $C_6H_5$—NH—CO | 57 d |
| Ex. 2 | $C_8H_{17}$—O— | $C_6H_5$—NH—CO | 58 d |
| Ex. 35 | $CH_3$—CO— | $C_6H_5$—NH—CO | 61 d |

We claim:

1. A polyalkylpiperidine compound of the formula I

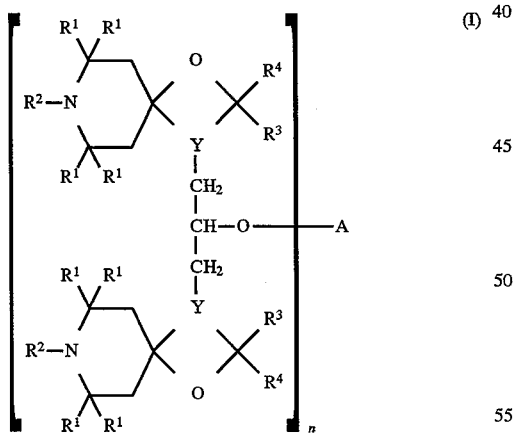
(I)

in which Y is the group

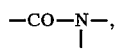

$R^1$ is a hydrogen atom or an alkyl group,
$R^2$ is a group of the formula $R^{17}$—O— or $R^{18}$—CO— (acyl),
$R^3$ and $R^4$ are identical or different and are a hydrogen atom or an alkyl group, or $R^5$ and $R^4$, together with the carbon atom connecting them, form a ring having 5 to 12 ring members or a group of the formula

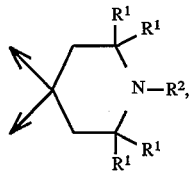

n is 1, 2 or 3, and

A, in the case where n=1, is a hydrogen atom, $R^5$—, $R^5$—CO—, $R^5$—NH—CO— (urethane), —$COOR^5$, —$P(OR^6)(OR^7)$, —$Si(OR^5)(OR^5)(OR^5)$, or —$SiR^5R^5R^5$ A, in the case where n=2, is —$R^{11}$—, —CO—$R^{12}$—CO—, —CO—NH—$R^{13}$—NH—CO—, —CO—, =$POR^5$, =Si$(OR^5)(OR^5)$, or =$SiR^5R^5$ A, in the case where n=3, is $R^{14}\equiv$, $R^{15}(CO—)_3$, $R^{16}$(NH—CO—)$_3$, $\equiv$Si$(OR^5)$, $\equiv$Si$R^5$ $R^5$ is a $C_1$-$C_{18}$alkyl group, a $C_2$-$C_{18}$-alkenyl group, a $C_2$-$C_{18}$-alkynyl group, a $C_5$-$C_{12}$-cycloalkyl group, a $C_6$-$C_{10}$-bicycloalkyl group, a $C_5$-$C_8$-cycloalkenyl group, a $C_6$-$C_{10}$-aryl group, a $C_7$-$C_9$aralkyl group, a $C_7$-$C_9$-alkaryl group, unsubstituted or substituted by $C_1$-$C_4$-alkyl or phenyl, where a plurality of radicals $R^5$ may be identical or different, $R^6$ and $R^7$ are identical or different and are a $C_1$-$C_{18}$-alkyl group, a $C_2$-$C_{18}$-alkenyl group, a $C_2$-$C_{18}$-alkynyl group, a $C_5$-$C_{12}$-cycloalkyl group, a $C_6$-$C_{10}$-bicycloalkyl group, a $C_5$-$C_8$-cycloalkenyl group, a $C_6$-$C_{10}$-aryl group, a $C_7$-$C_9$-aralkyl group or a $C_7$-$C_9$-aralkyl group, substituted by $C_1$-$C_4$-alkyl or phenyl, or $R^6$ and $R^7$ together are a radical of the formula II or III

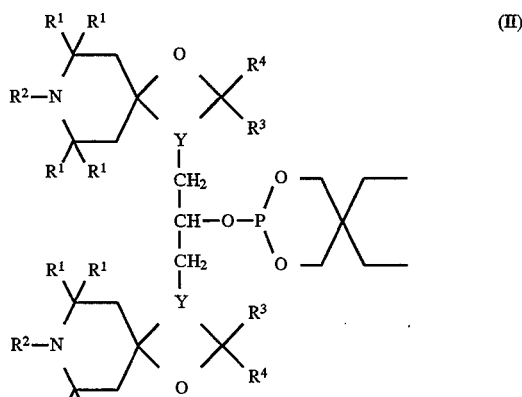
(II)

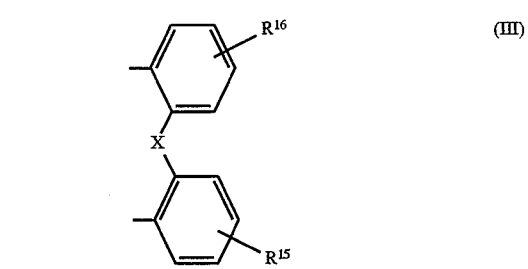
(III)

in which $R^1$, $R^2$, $R^3$, $R^4$ and $R^5$ are as defined above, and X is a direct bond or methylene group or a 1,1-alkylidene group having 2 to 5 carbon atoms, $R^{11}$, $R^{12}$ and $R^{13}$ are identical or different and are a $C_1$–$C_{12}$-alkylene group, a $C_5$–$C_7$-cycloalkylene group, a $C_8$–$C_{10}$-bicycloalkylene group, a $C_6$–$C_{10}$-arylene group, a $C_7$–$C_9$-aralkylene group or $C_7$–$C_9$-arylene group, substituted by $C_1$–$C_4$-alkyl or phenyl, $R^{14}$, $R^{15}$ and $R^{16}$ are identical or different and are a trifunctional $C_3$–$C_{18}$-alkyl radical, $C_5$–$C_7$-cycloalkyl radical, $C_6$–$C_{10}$-aryl radical or $C_6$–$C_{10}$-aryl radical which is substituted by $C_1$–$C_4$-alkyl or phenyl, $R^{17}$ and $R^{18}$ are identical or different and are a $C_1$–$C_{10}$-alkyl group, a $C_5$–$C_7$-cycloalkyl group or a $C_6$–$C_{10}$-aryl group.

2. A compound as claimed in claim 1, wherein $R^1$ in the formula I is a methyl group.

3. A compound as claimed in claim 1, wherein $R^2$ in the formula I is a $C_1$–$C_{18}$-acyl group.

* * * * *